(12) United States Patent
Fleury et al.

(10) Patent No.: US 7,642,774 B2
(45) Date of Patent: Jan. 5, 2010

(54) METHOD FOR FAST MEASUREMENT OF THE SATURATION AND THE RESISTIVITY OF A POROUS MEDIUM

(75) Inventors: Marc Fleury, La Celle-Saint-Cloud (FR); Mei Han, Paris (FR)

(73) Assignee: Institut Francais du Petrole, Rueil-Malmaison Cedex (FR)

( * ) Notice: Subject to any disclaimer, the term of this patent is extended or adjusted under 35 U.S.C. 154(b) by 0 days.

(21) Appl. No.: 12/204,932

(22) Filed: Sep. 5, 2008

(65) Prior Publication Data

US 2009/0066335 A1 Mar. 12, 2009

(30) Foreign Application Priority Data

Sep. 7, 2007 (FR) .................................. 07 06288

(51) Int. Cl.
*G01V 3/00* (2006.01)
(52) U.S. Cl. ..................... 324/303; 324/306; 324/307
(58) Field of Classification Search ......... 324/300–376; 702/6, 7, 13, 10; 73/38, 152.08
See application file for complete search history.

(56) References Cited

U.S. PATENT DOCUMENTS

| | | | | | |
|---|---|---|---|---|---|
| 2,938,708 | A | * | 5/1960 | Arps .......................... 175/50 |
| 2,945,175 | A | * | 7/1960 | Egan .......................... 324/367 |
| 3,213,356 | A | * | 10/1965 | Brown et al. .................. 324/303 |
| 3,213,357 | A | * | 10/1965 | Brown et al. .................. 324/303 |
| 3,237,094 | A | * | 2/1966 | Blackburn et al. .......... 324/323 |
| 4,281,289 | A | * | 7/1981 | Donaldson et al. .......... 324/355 |
| 4,413,512 | A | * | 11/1983 | Zemanek, Jr. ............. 73/152.08 |
| 4,752,882 | A | * | 6/1988 | Givens ........................ 702/13 |

(Continued)

FOREIGN PATENT DOCUMENTS

EP 0 586 001 A1 3/1994

(Continued)

OTHER PUBLICATIONS

Fleury, M. et al:"A New Approach to Derive Relative Permeability Data While Measuring Resistivity Indes", International Symposium of the Society of Core Analysts, Aug. 2005, XP002474993, Toronto.

(Continued)

*Primary Examiner*—Brij B. Shrivastav
*Assistant Examiner*—Tiffany A Fetzner
(74) *Attorney, Agent, or Firm*—Antonelli, Terry, Stout & Kraus, LLP.

(57) ABSTRACT

A method for measuring the conducting fluid saturation and the resistivity of a porous medium have application to development of underground geological formations. A solid sample is extracted from the medium and placed in a centrifugation cell, beside a second sample for limiting the capillary end effect in the first sample. The two samples are partly desaturated by subjecting them to centrifugation. The resistivity of the sample is measured by placing it in a radial-electrode resistivity measurement cell. The saturation of the sample is then determined by measuring its nuclear magnetization by means of an NMR device. Repeating this procedure for different centrifugation velocities provides resistivity and saturation pairs allowing a relationship between saturation and resistivity to be estimated.

5 Claims, 5 Drawing Sheets

U.S. PATENT DOCUMENTS

| | | | | |
|---|---|---|---|---|
| 4,926,128 A * | 5/1990 | Givens | | 324/376 |
| 5,164,672 A * | 11/1992 | Gilliland et al. | | 324/376 |
| 5,209,104 A * | 5/1993 | Collins et al. | | 73/38 |
| 5,557,200 A * | 9/1996 | Coates | | 324/303 |
| 6,005,389 A * | 12/1999 | Prammer | | 324/303 |
| 6,088,656 A * | 7/2000 | Ramakrishnan et al. | | 702/13 |
| 6,229,308 B1 * | 5/2001 | Freedman | | 324/303 |
| 6,400,148 B1 * | 6/2002 | Meyer et al. | | 324/303 |
| 6,470,274 B1 * | 10/2002 | Mollison et al. | | 702/7 |
| 6,844,729 B2 * | 1/2005 | Herron et al. | | 324/303 |
| 6,856,132 B2 * | 2/2005 | Appel et al. | | 324/303 |
| 6,879,154 B2 * | 4/2005 | Fleury | | 324/303 |
| 7,221,165 B2 * | 5/2007 | Fleury | | 324/303 |
| 7,363,161 B2 * | 4/2008 | Georgi et al. | | 702/7 |
| 7,532,983 B2 * | 5/2009 | Montaron | | 702/7 |
| 2004/0090230 A1 * | 5/2004 | Appel et al. | | 324/307 |
| 2005/0104596 A1 * | 5/2005 | Fleury | | 324/376 |
| 2006/0273788 A1 * | 12/2006 | Georgi et al. | | 324/303 |
| 2007/0132451 A1 * | 6/2007 | Ramakrishnan | | 324/303 |
| 2007/0276639 A1 * | 11/2007 | Montaron et al. | | 703/10 |
| 2008/0120034 A1 * | 5/2008 | Georgi et al. | | 702/6 |
| 2008/0154509 A1 * | 6/2008 | Heaton | | 702/7 |
| 2009/0066335 A1 * | 3/2009 | Fleury et al. | | 324/333 |

FOREIGN PATENT DOCUMENTS

| | | |
|---|---|---|
| EP | 1 398 630 A1 | 3/2004 |
| EP | 1 729 151 A1 | 12/2006 |
| FR | 2 844 355 | 3/2004 |
| FR | 2 864 244 | 6/2005 |

OTHER PUBLICATIONS

Huang, David D., et al:"Capillary End Effects in Coreflood Calculations", 1996 SCA Conference Paper No. 9634, pgs. 1-10.

* cited by examiner

METHOD FOR FAST MEASUREMENT OF THE SATURATION AND THE RESISTIVITY OF A POROUS MEDIUM

BACKGROUND OF THE INVENTION

1. Field of the Invention

The present invention relates to the petrophysical field and more particularly to the determination of brine saturation within a porous medium such as a geological formation.

2. Description of the Prior Art

Knowledge of the brine saturation allows calculation of the amount of hydrocarbons in place in the case of an oil reservoir, or the amount of $CO_2$ stored in the case of $CO_2$ storage. It is therefore very important for the specialist in charge of the development of an underground formation, within the context of hydrocarbon production or acid gas storage for example, to know the brine saturation of the formation.

It is well known to determine the saturation of a geological formation by carrying out electrical measurements within wells, while drilling or not. These measurements in a well are referred to as well logs. These electrical logs measure the electrical resistivity of the medium. They have to be analyzed in order to deduce the saturation values of the formation.

A conventional method for carrying out such a resistivity log interpretation uses Archie's laws, and notably the following relation:

$$RI = \frac{R_t}{R_0} = S_w^{-n}$$

with:

RI: resistivity index
$S_w$: brine saturation of the medium
$R_t$: electrical resistivity of the medium
$R_0$: electrical resistivity of the 100° brine-saturated medium ($S_w=1$)
n: an integer.

The electrical resistivity of the medium $R_t$ is measured by electrical logging, whereas the electrical resistivity of the 100% brine-saturated medium $R_0$ is determined from measurements performed on cores.

An important stage in the interpretation of resistivity logs ($R_t$) in terms of brine saturation ($S_w$) is defining parameter n of the above relationship.

It is therefore well known to measure, on the one hand, the resistivity index and the brine saturation on samples taken from the geological formation. These measurements are often carried out under the pressure and temperature conditions encountered within the formation. Thus, by measuring several pairs (RI, $S_w$), parameter n of Archie's relation can be estimated.

Measurement of the resistivity index of a porous medium is the most difficult experimental stage in this interpretation of the electrical response of porous media.

A possible technique for measuring the resistivity index and the brine saturation on a large number of samples places these samples on a semi-water permeable porous plate arranged in an enclosure that can be pressurized. When pressure P in the enclosure is progressively increased, the saturation of the samples decreases progressively. At each pressure stage, the samples are removed from the enclosure and the saturation is determined by weighing. The resistivity is measured by applying two metallic plates connected to a measuring device onto the two faces of the sample.

However, it is known that saturation determination by means of this technique is destroyed by errors due to a loss of grains of the sample during the experiment and that the resistivity measurement is destroyed by errors due to the contact resistances between the plates and the porous medium.

Furthermore, for low-permeability samples, a porous plate of very low permeability is necessary, requiring long experimental times (of the order of 2 months at least).

SUMMARY OF THE INVENTION

The invention is an alternative method for measuring a conducting fluid saturation and a resistivity of a porous medium, initially saturated with the fluid. The method comprises the following stages:

a) extracting at least a first solid sample from the medium;

b) placing the first sample into a centrifugation cell, beside a second sample for limiting a capillary drag in the first sample, the samples being arranged next to one another to optimize capillary contact between them;

c) partly desaturating the first and second samples by subjecting the samples in the centrifugation cell to centrifugation with a predetermined rotating speed and a sufficient rotation time allowing desaturation of the first sample;

d) measuring the resistivity of the first sample by placing it in a resistivity measurement cell for injecting an electrical current using at least a first pair of electrodes and measuring an electrical potential between at least a second pair of electrodes, the electrodes being radially disposed around the first sample; and e) determining the saturation of the first sample by measuring a nuclear magnetization of the sample using an NMR device.

According to the invention, the second sample can be extracted directly from the porous medium from which the first sample was taken. Capillary contact can be optimized by inserting a fluid wet membrane between the two samples.

The method can be used to estimate a relationship permitting determination of the saturation as a function of the resistivity. Stages b) to e) are therefore repeated while modifying the rotating speed so as to obtain pairs of resistivity and saturation values for the first sample. The relationship is then estimated from these pairs.

Finally, this relationship can be used to measure the conducting fluid saturation of an underground formation. The method then comprises the following stages:

extracting samples from the formation and saturating them with the fluid determining a relationship for determining the saturation as a function of the resistivity for each sample, using the method described above;

selecting samples so that each sample has a different relationship than the other samples;

measuring the resistivity index and the fluid saturation of each sample, using a method utilizing temperature and pressure conditions representative of the underground formation;

performing at least one electrical resistivity logging operation through the formation;

determining from the at least one electrical resistivity operating fluid saturation in the formation by applying the relationship.

BRIEF DESCRIPTION OF THE DRAWINGS

Other features and advantages of the method according to the invention will be clear from reading the description hereafter of embodiments given by way of non limitative example, with reference to the accompanying figures wherein.

DETAILED DESCRIPTION OF THE INVENTION

The method according to the invention allows fast measurement of the conducting fluid saturation and the resistivity index of a porous medium, Usually, these measurements are performed in order to obtain extremely reliable measurements, regardless of the time required to perform them. On the contrary, the method according to the invention provides a method allowing these measurements to be rapidly obtained without any precision loss.

The measuring method is described within the context of a medium containing the following two fluids: brine and air. However, the method is also applicable to a medium containing brine and oil, such as a petroleum reservoir for example, and even to any medium containing at least one conducting fluid.

Figure 1:
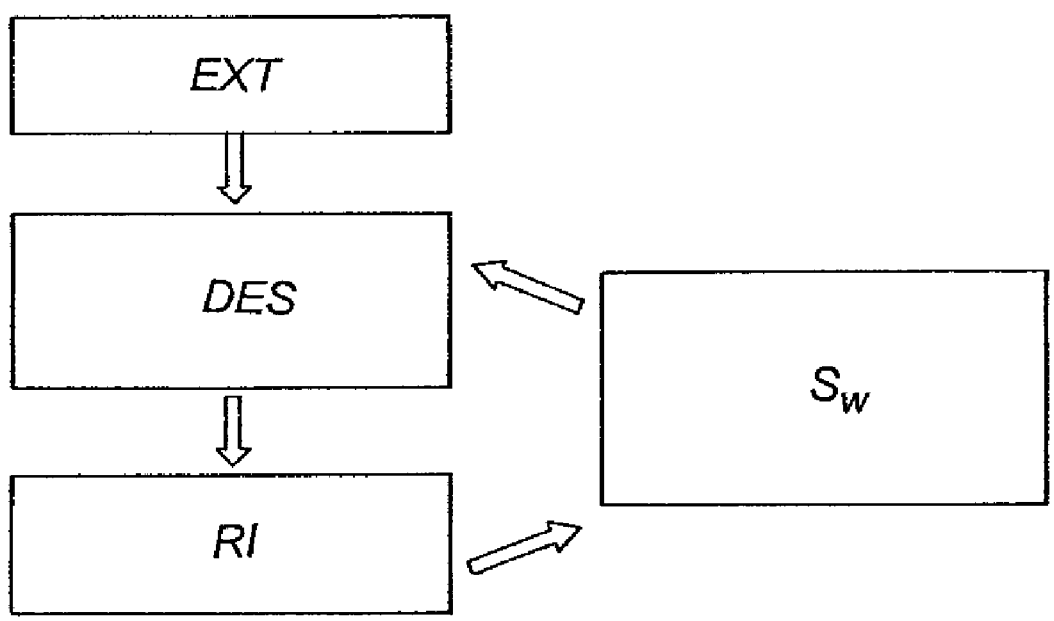
FIG. 1 diagrammatically shows the stages of the method allowing fast measurement of the conducting fluid saturation and the resistivity of a porous medium.

For a medium containing brine (conducting fluid) and air, and initially saturated with the brine, the following procedure, described in FIG. 1, is applied:

extracting at least one solid sample from the medium (generally a core)—EXT partly desaturating the sample by centrifugation—DES measuring the resistivity index by radial measurement—RI measuring the saturation by means of an NMR device—$S_w$.

1—Partial Desaturation of the Sample

The goal of the procedure of FIG. 1 is to obtain a mean saturation SW in the sample. The technique used drains the sample by centrifugation, within a predetermined period of time, and according to a predetermined rotating speed ω, so as to partly desaturate the sample until a particular but unknown saturation value $S_w$ is obtained.

Figure 2:
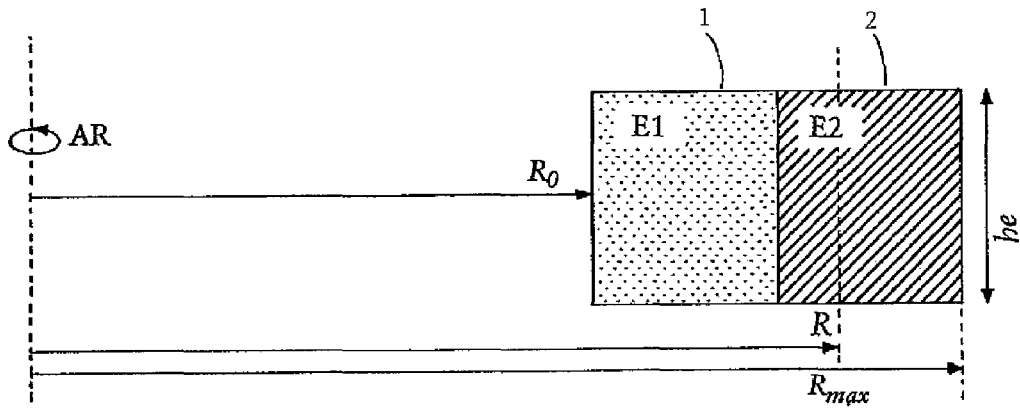
FIG. 2 diagrammatically shows the implementation of the desaturation by centrifugation according to the invention.

FIG. 2 diagrammatically shows the implementation of the desaturation by centrifugation according to the invention. The axis of rotation of the centrifuge (AR) is shown on the left. By way of example, the lengths of the samples are identical (0.03 m), as well as their heights (diameters in the case of cylindrical cores) (he=0.04 m). Distance R represents a distance in relation to axis of rotation (AR). Two particular values are given in FIG. 2: distance $R_0$ is the distance between this axis and the sample placed in the centrifugation cell, as close as possible to axis AR, that is sample 1 (E1); distance $R_{max}$ represents the distance between axis of rotation (AR) and the furthest end of sample 2 (E2). According to an example, $R_{max}$=0.263 m.

When a sample saturated with a first fluid is centrifuged in another second fluid of different density, a pressure difference ΔP appears, producing a change in the saturation of the sample. The pressure difference generated depends on distance R to the center of rotation, on rotating speed X and on the fluid densities. This pressure is given by:

$$\Delta P(R) = \frac{1}{2}\omega^2(R_{max}^2 - R^2)(\rho_w - \rho_g) \quad (1)$$

where $\rho_w$ and $\rho_g$ are the densities of the two fluids (brine, air in these experiments) and $R_{max}$. When the pressure generated (Eq. 1) linked with the rotation is higher than the capillary pressure, the brine flows. The brine saturation decreases until equilibrium is obtained when the flow rate is zero. At equilibrium and for a given pressure, the saturation is given by the capillary pressure curve.

Different saturations are obtained by carrying out centrifugation at various rotating speeds. It is however not necessary to reach capillary equilibrium.

Figure 3:
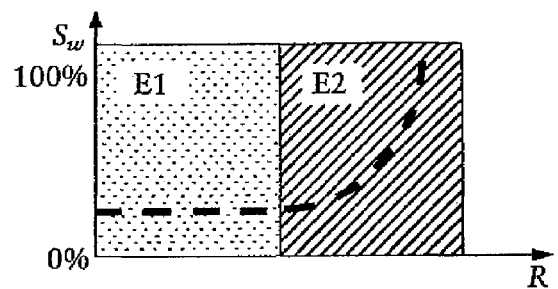
FIG. 3 diagrammatically illustrates a saturation profile SW in samples E1 and E2 in capillary contact occurring with centrifugation in a device according to FIG. 2.

According to Equation (1), the maximum pressure (lowest saturation) is obtained at the inlet face ($R_0$ in drainage) of the fluid of lower density. At the outlet face, the capillary pressure is zero and the saturation is thus theoretically one. The zone of high saturation constitutes the capillary end effect. Because of this pressure inhomogeneity, the saturation profile is not uniform along the axis of rotation, as diagrammatically shown in FIG. 3 illustrating a saturation profile $S_w$ in samples E1 and E2 in capillary contact, as a function of radius R.

In order to avoid measurement interpretation problems, linked with the non-uniform saturation in the sample, two neighboring samples from the same core are for example superposed. The mean saturation and resistivity values of the first sample are then measured.

Figure 4:
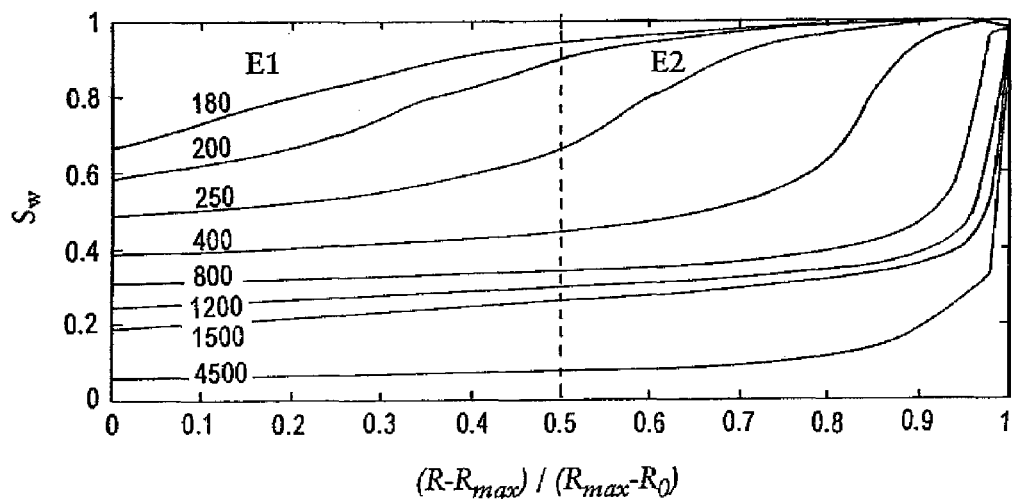
FIG. 4 shows saturation profiles SW in samples E1 and E2 for various centrifuge rotating speeds.

Good capillary contact with the second sample is necessary for first sample sample to have a uniform saturation profile. A brine wet membrane can thus be used between the two samples. Also, the diameter of first sample is preferably not larger than the diameter of second sample (he, FIG. 2). Saturation profiles as shown in FIG. 4 are typically obtained. This FIG. 4 shows saturation profiles SW in samples E1 and E2 as a function of a normalized length (($R-R_{max}$)/($R_{max}-R_0$)), for different centrifuge rotating speeds (from 180 rpm (upper curve) to 4500 rpm (lower curve)).

The second sample can however be replaced by another sample from another medium, provided that its porosity and permeability are substantially identical to those of the first sample.

Thus, according to the invention, the first sample is desaturated in a centrifugation cell, beside a second sample for limiting the capillary end effect in first sample. The samples are therefore arranged side by side, the second sample being the furthest from the center of rotation of the centrifuge. Furthermore, the samples must be arranged so as to optimize capillary contact between them. These two samples are then partly desaturated by subjecting them to centrifugation with a predetermined rotating speed and a sufficient rotation time to allow desaturation of the first sample (and therefore of the second sample).

2—Measurement of Resistivity Index RI of the Sample Device

Figure 5A:
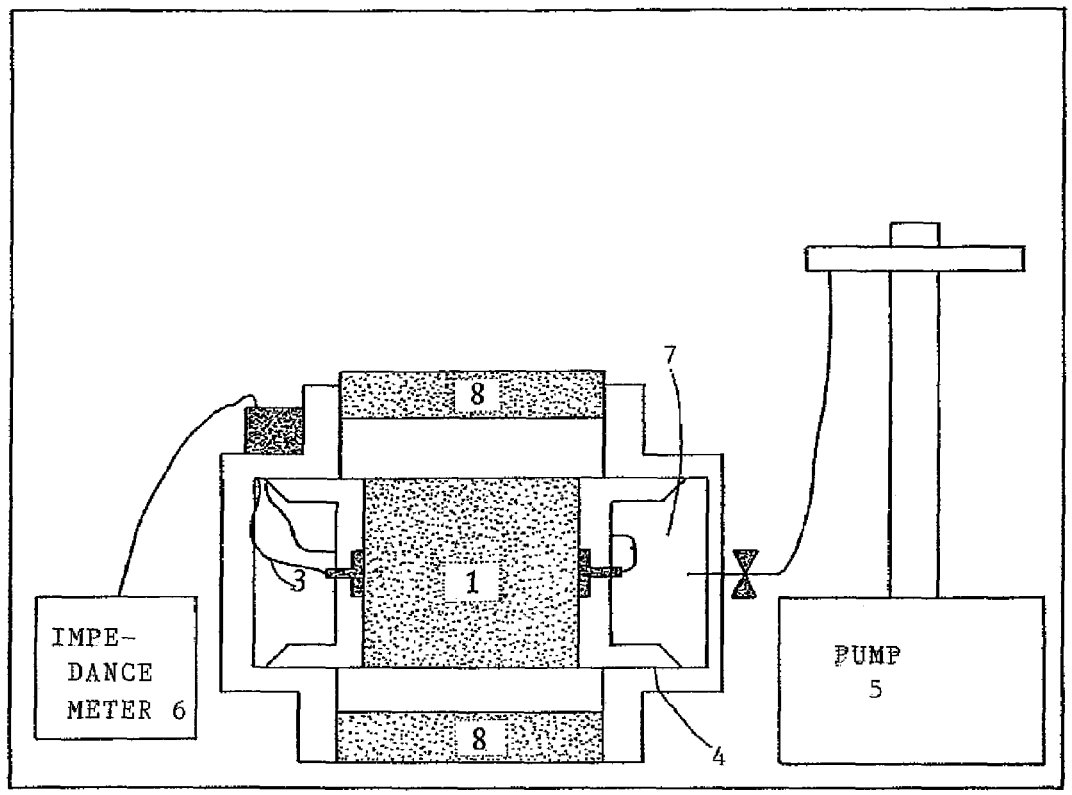
FIGS. 5A and 5B show a radial resistivity measurement device.
Figure 5B:
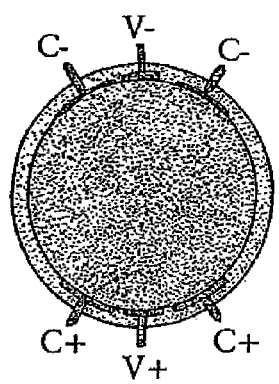

The resistance is measured in a radial-electrode resistivity measurement cell. Such a device is described in EP Patent 0,701,128 and French Patent 2,781,573. The cell has electrodes radially arranged around the sample. A device comprising six electrodes, as described in FIG. 5A, can for example be used. FIG. 5B is a vertical projection of the cell and of the electrodes. The procedure is described with reference to these figures.

Two pairs of electrodes C+ and C− inject a current into first sample 1 and another pair of electrodes V+ and V− measure the electrical potential. They are connected to the potential and current inlets of an impedance meter via electrical wires.

In order to prevent the sample from drying while measuring, brine-saturated foams 8 are disposed at the top and at the bottom to maintain a high moisture content of the air in contact with the sample.

One of the difficulties in using this type of device is that good electrical contact has to be achieved with the sample. Besides, this contact has to be reproducible for the measurements themselves to be reproducible.

The electrodes are cast or inserted in an elastomer sheath 4 allowing a confining pressure to be applied. It can be a Viton sheath for example. The confinement fluid contained in compartment 7 is connected to a pump 5 filled with a viscous oil intended to apply a confining pressure set at 30 bars. This pressure allows good electrical contact to be obtained between the electrodes and the sample, consequently the electrical fields in the sample remain quasi-constant between the various measurements on a single sample. This guarantees a constant measurement condition for the resistivity index.

A second commonly encountered problem is the grain loss from the sample while handling the sample, leading to measurement errors.

According to the invention, in order to remove the sample 1 without damaging it after electrical measurements, sheath 4 and pump 5 are advantageously used. In fact, the pump 5 can remove the oil in the cell and thus produce an electrode spacing allowing the sample to be removed without slipping.

Measurement

A current is injected between electrodes C+ and C−, a potential is measured between contacts V+ and V−, and the resistance R=U/I is deduced.

The real part and the imaginary part of the resistance are measured at several frequencies. Measurement is performed with an impedance meter that determines the complex impedance and is therefore not affected by the capacitive effects (imaginary part). The real part is generally taken at 1 kHz to calculate the resistivity index. The imaginary part is used to evaluate the measurement reliability. At 1 kHz, it has to be about 10 times lower than the real part. Measurement is stabilized for about ten minutes after applying the confining pressure.

3—Saturation Measurement

The sample is removed from the device and then the saturation is measured by means of an NMR device that measures the nuclear magnetization. Such a device is well known.

An atomic nucleus can absorb the electromagnetic radiations of a specific frequency in the presence of a magnetic field. This phenomenon is referred to as Nuclear Magnetic Resonance (NMR). In the description of the invention, the hydrogen nucleus is considered present in the brine.

A proton can move to a higher energy level if it absorbs an amount of energy at the Larmor frequency CO, the latter being linked with the magnetic field $B_0$ wherein the sample is arranged:

$$\Delta E = \hbar \omega \text{ and } \omega = \gamma B_0 \qquad (3)$$

where $\hbar$ is the Planck's constant divided by $2\pi$. $\gamma$ is the gyromagnetic ratio of the nucleus considered. $B_0$ is a static magnetic field along axis Z. Another oscillating magnetic field $B_1$ is applied in plane XY. When the frequency of $B_1$ is close to $\omega$ the protons which are irradiated to the highest energy level.

The return of the protons to the lower energy level after the suppression of field $B_1$ is referred to as relaxation. The characteristic times required for a nucleus to return to equilibrium are the spin-network relaxation time denoted by $T_1$ and the spin-spin relaxation time $T_2$. $T_2$ is generally measured.

The NMR device measures the global nuclear magnetization M(t) returning to equilibrium as a function of time by means of the CPMG sequence. Spin-spin relaxation T2 is decomposed into a sum of exponentials such that:

$$M(t = 2n_j\tau) = \sum_i A_i \exp\left(-\frac{2n_j\tau}{T_{2i}}\right) n_j = 1 \ldots n \qquad (4)$$

The main acquisition parameters are: $\tau$, inter-echo half-time, for example 60 microseconds, and n, number of echoes or measuring points (varying according to the samples).

As far as possible, a signal-to-noise ratio above 100 is desirably reached.

In general, measurement of the total magnetization allows direct obtaining of the pore volume Vp by comparing the signal with a known amount of brine $V_{standard}$ $$V_p = \frac{Mi(Sw = 100\%)}{Mi(\text{standard brine})} \times V_{standard} \qquad (5)$$

where Mi is the magnetization M(t=0).

In the brine-air system, the air produces no NMR signal and the saturations Sw are directly obtained during centrifugation or imbibition by calculating the ratio of magnetizations Mi according to:

$$S_w = \frac{Mi(Sw)}{Mi(Sw = 100\%)} \qquad (6)$$

The method according to the invention thus measures, by means of an NMR device, the nuclear magnetizations, then using equation (6). Mi(Sw=100%)) therefore has to be known. Since samples are saturated at the start of the method, it is necessary to carry out a nuclear magnetization measurement prior to the desaturation stage.

Measurement Examples

1) Fontainebleau Sandstone

Figure 6:
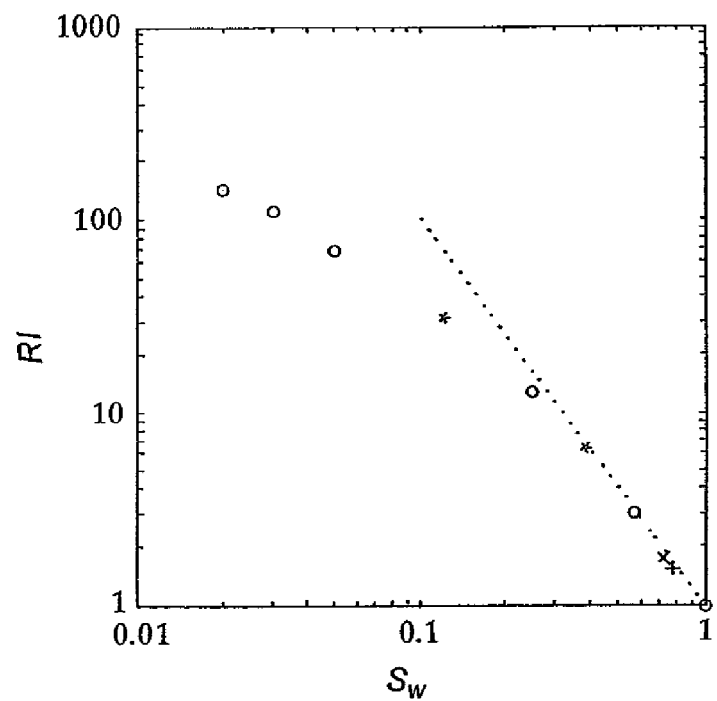
FIG. 6 shows an example of resistivity index and saturation measurement results for two Fontainebleau sandstones of high permeability.

FIG. 6 shows the result of resistivity and brine saturation measurements on two Fontainebleau sandstones of high permeability (1000 mD). Good coherence is observed between the two samples. The slope of the curve $RI = S_w^{-n}$ is close to 2 above a saturation of about 0.20. The method allows showing that, below 0.20, a slope change is observed, which is interpreted as the start of a film-dominated conduction regime.

2) Bimodal Structure Limestone, Case 1

Figure 7:
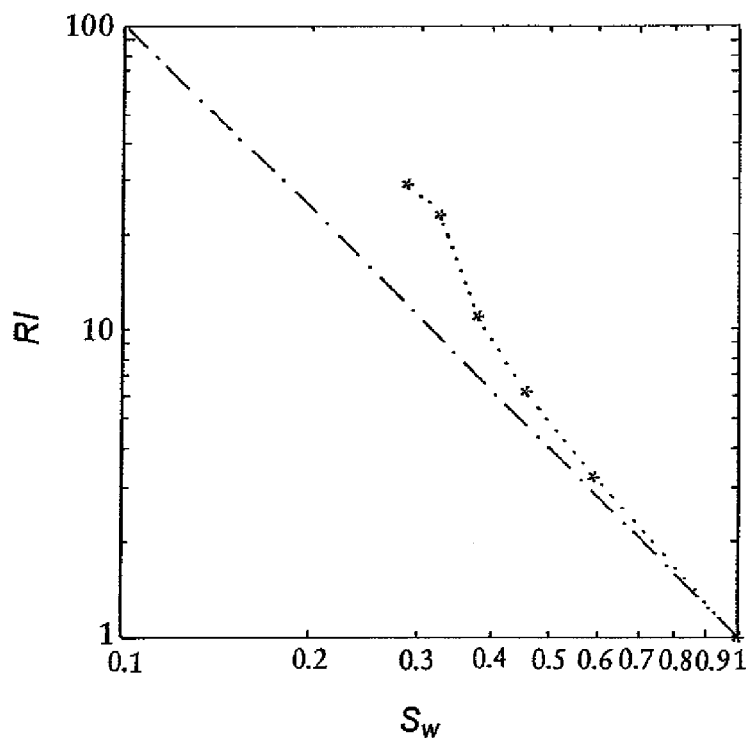
FIG. 7 shows resistivity index and saturation measurements on a limestone with a bimodal structure in drainage.

In a complex structure such as a limestone containing two pore sizes shown in FIG. 7, the resistivity index curve shows a particular behavior: an upward deviation is observed. The saturation profiles show that the saturation is uniform in the various saturation stages. The relaxation time distributions show two modes corresponding each to a pore size distribution. When the porous system is partly desaturated, it can be seen that the larger pores are emptied first, whereas the smaller pores remain completely saturated up to a mean saturation of 0.38.

3) Bimodal Structure Limestone, Case 2

Figure 8:
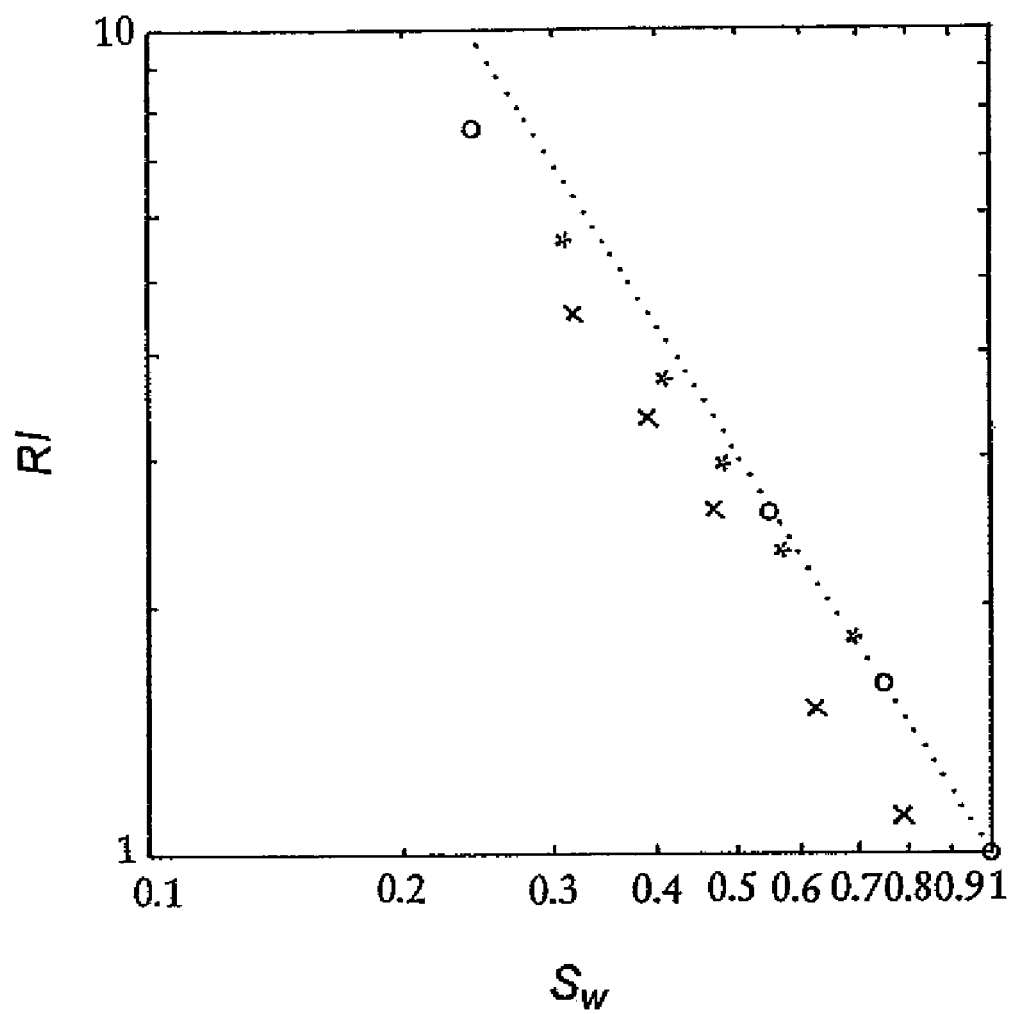
FIG. 8 shows resistivity index and saturation measurements on a limestone with a bimodal structure in drainage.

In the case of this limestone shown in FIG. 8, the resistivity index curve shows no significant anomalies. There is a low hysteresis in imbibition. The relaxation times show that the two populations are emptied at the same time in this case. In imbibition, the large pores remain empty.

PARTICULAR EMBODIMENTS

According to an embodiment, the measurements performed on the samples are completed by a relaxation time distribution measurement using an NMR device. These distribution measurements are intended to determine the pores emptied for a given pressure. This influences the electrical response. The use of NMR techniques thus complements the information obtained and it is useful for electrical response interpretation. In fact, in complex structures comprising several pore size populations (by microporosity and macroporosity), the way the various populations drain themselves influences the electrical response.

The relaxation time distribution gives information on the pore size distribution according to the relationship:

$$\frac{1}{T_2} = \rho_2 \frac{S_p}{V_p} + \frac{1}{T_{2B}} \tag{7}$$

where $\rho_2$ is the surface relaxivity coefficient and $T_{2B}$ the specific relaxation time of the brine. The relaxation time $T_2$ of a pore is linked with its surface to volume ratio (Sp/Sv). The distribution of $T_2$, calculated according to Equation 4, shows the distribution of the V/S ratio in the pore network, referred to as "pore size" distribution. This is true in case of a slow exchange between the pores. Thus, the longest relaxation times correspond to the larger pores.

In the brine-air system, relaxation time $T_2$ of a partly saturated sample is linked with the surface wetted by water $S_m$ and the saturation $S_{wp}$ of this pore:

$$\frac{1}{T_2} = \rho_2 \frac{S_m}{V_p * S_{wp}} + \frac{1}{T_{2B}} \tag{8}$$

According to another embodiment, the measurements performed on the cores are completed by a saturation profile measurement. These saturation profile measurements allow knowing if the saturation is uniform or not: if samples 1 and 2 are not in capillary contact, there is a saturation profile on sample 1 similar to sample 2. The measurements then have to be repeated while improving the capillary contact between the samples.

Using the results of a well-known mercury injection measurement allows predicting the saturation profile as a function of the rotating speed. Assuming that the sample is wet with water, the conversion relation is as follows:

$$P_{brine-air} = P_{Hg} \frac{\gamma_{brine-air} \cos\theta_{brine-air}}{\gamma_{Hg} \cos\theta_{Hg}}$$

where $\gamma$ is the surface tension and $\theta$ the angle of contact, the subscripts designating the mercury (Hg)-air system and the air-brine system. In a position and at a rotating speed given by Equation (1), the pressure obtained is calculated and the corresponding saturation is sought in the air-brine capillary pressure curve. This allows finding the local saturation in each position R and thus obtaining the saturation profiles (FIG. 4). It can be seen that, in sample 1, the saturation is quasi-uniform and that the capillary foot is contained in sample 2.

Saturation Profile

The saturation profile is measured with a standard NMR imaging sequence (pulsed-gradient Hahn echo sequence). When a field gradient is applied, the magnetic field varies linearly along the direction of the gradient. The Larmor frequency of the protons varies proportionally along the magnetic gradient.

$$\omega(y) = \gamma B_0(1 + Gy) \tag{9}$$

The local frequency codes the position of the protons in the direction of the gradient. By relating the measured proton density and the positions, the protonic density profile $d_p(z)$ along the direction of the gradient is obtained.

In the brine-air system, measurement of the density profile $d_p(z)$ allows saturation profile $S_w(z)$ to be obtained:

$$S_w(z) = \frac{dp(z)}{dp(z, Sw = 100\%)} \tag{10}$$

According to another embodiment, centrifugation drainage is replaced by spontaneous imbibition. The sample is then put in a beaker to which a controlled amount of brine is added. The brine then spreads through the whole sample. The different saturation stages in imbibition can be obtained by repeating this operation. The inlet face of the brine in imbibition corresponds to the outlet face of the brine in drainage. The sample and the brine are at atmospheric pressure. The electrical measurement and NMR measurement processes are the same as in drainage.

Applications of the Measurement Technique According to the Invention

According to an embodiment of the invention, the method allowing fast measurement of the saturation and of the resistivity index of a porous medium can be used to define a relation allowing determining the saturation as a function of the resistivity.

Several measurements are therefore performed from the same sample coming from this medium. At the end of the first series of measurements, the sample is put back into the centrifuge so as to obtain another saturation stage. Rotating speed ω is then modified. The measuring stages are then repeated so as to obtain different saturations, and the resistivity index and the saturation are measured for each one of these saturations.

Several pairs of resistivity values (RI) and of saturation values ($S_w$) are thus obtained for the studied sample.

A relation allowing determining the saturation as a function of the resistivity is estimated from these pairs. It is possible, for example, to use Archie's law and to determine, by means of these pairs, the value of index n:

$$RI = S_w^{-n}$$

with:
RI: resistivity index
$S_w$: brine saturation of the medium
n: an integer.

According to another embodiment, the method can be applied to the determination of the brine saturation (conducting fluid) of an underground formation, such as a petroleum reservoir or a gas storage reservoir, by interpreting electrical measurements such as logs. In fact, this new measurement method allows very fast characterization of a large number of samples at a low cost as a result of the use of a centrifuge and of a simple electrical assembly. Although it does not allow exploring pressure and temperature domains close to the reservoir, it is useful to establish a reference curve under simplified conditions to evaluate thereafter, with more constraining techniques, the pressure and temperature effects. Thus, the method can be used in order to select the samples, prior to more precise interpretation under the pressure and temperature conditions of the formation. The method then comprises the following stages:

Samples are taken from the formation and saturated with brine. A relation allowing deducing the saturation as a function of the resistivity for each sample is then determined using the above method. Samples are then selected so that each one has a different relation from the other samples. For example, if Archie's law is used, a value of index "n" is estimated for each sample. All the samples having a common relation, that is with an equal value for "n", are grouped together. A single one is then selected from this sample family. The selected samples are representative of a particular correlation between the saturation and the resistivity. The resistivity index and the brine saturation of each selected sample are then measured by means of a method suited for working according to temperature and pressure conditions specific to the underground formation. The method described in Fleury M., "*Advances in Resistivity Measurements using the FRIM Method at Reservoir Conditions. Applications to Carbonates*". Proceedings of the International Symposium of the Society of Core Analysts, September 2003, Pau, FRANCE, can for example be used. Finally, the saturation of the underground formation is deduced by applying the relation to at least one electrical resistivity log measured through the formation. The various relations are applied as a function of the depth of the log and of the corresponding sample, or through grouping of the various measurements, referred to as "rock typing", not necessarily related to the depth in a simple manner.

The invention claimed is:

1. A method for determining saturation of a conducting fluid as a function of resistivity in a porous medium initially saturated with the conducting fluid, comprising:
a) extracting at least a first solid sample from the medium;
b) placing the first sample into a centrifugation cell, beside a second solid sample which limits a capillary end effect in the first sample, the samples being arranged next to one another in order to optimize capillary contact therebetween;
c) partly desaturating the first and second samples by centrifugation of the samples in the centrifugation cell with a rotating speed and rotation time allowing desaturation of the first sample;
d) measuring resistivity of at least the first sample by placing at least the first sample in a resistivity measurement cell and providing an electrical current using at least a first pair of electrodes and measuring an electrical potential between at least a second pair of electrodes, the first and second pairs of electrodes being radially disposed around at least the first sample;
e) determining fluid saturation of at least the first sample by measuring a nuclear magnetization of the first sample using a Nuclear Magnetic Resonance (NMR) device; and
f) repeating steps b) to e) while modifying the rotating speed of the centrifugation cell in order to obtain pairs of resistivity and saturation values for at least the first sample; and
g) using the pairs of resistivity and saturation values for estimating a relationship between the saturation and the resistivity value of at least the first sample.

2. A method as claimed in claim 1, wherein the second sample is extracted from the porous medium.

3. A method as claimed in claim 1, wherein capillary contact is optimized by inserting a membrane, wettable by the fluid, between the first and second samples before step c) is performed.

4. A method as claimed in claim 2, wherein capillary contact is optimized by inserting a membrane, wettable by the fluid, between the first and second samples before step c) is performed.

5. A method in accordance with claim 1 for measuring conducting fluid saturation of an underground formation comprising:
extracting multiple solid samples from the underground formation and saturating the solid samples with the conducting fluid, determining a relationship between saturation and resistivity values of each of the saturated solid samples and selecting samples such that the relationships of each of the saturated solid samples are different;
measuring the resistivity as in step d), and the fluid saturation of each of the selected solid samples as in step e), using temperature and pressure conditions chosen according to the underground formation;
performing at least one electrical resistivity logging operation through the underground formation; and
determining from the performed logging operation and the different relationships of the saturated solid samples, the conducting fluid saturation of the underground formation.

* * * * *